(12) United States Patent
Pinkowski et al.

(10) Patent No.: US 7,033,483 B2
(45) Date of Patent: Apr. 25, 2006

(54) FLUORIDE-SENSITIVE ELECTRODE

(75) Inventors: Alexander Pinkowski, Heidelberg (DE); Michael Wittkampf, Dossenheim (DE)

(73) Assignee: Prominent Dosiertechnik GmbH, (DE)

( * ) Notice: Subject to any disclaimer, the term of this patent is extended or adjusted under 35 U.S.C. 154(b) by 367 days.

(21) Appl. No.: 10/423,668

(22) Filed: Apr. 25, 2003

(65) Prior Publication Data

US 2003/0221961 A1    Dec. 4, 2003

(30) Foreign Application Priority Data

Apr. 27, 2002    (DE) ................................ 102 18 935

(51) Int. Cl.
*G01N 27/333*    (2006.01)

(52) U.S. Cl. .................................... 205/778.5; 204/419

(58) Field of Classification Search ........ 204/416–418, 204/419; 205/789, 778.5, 779
See application file for complete search history.

(56) References Cited

U.S. PATENT DOCUMENTS

| | | |
|---|---|---|
| 3,446,726 A | 5/1969 | Pungor et al. |
| 4,021,325 A | 5/1977 | Pungor et al. |
| 4,931,172 A | 6/1990 | Kobos et al. |

FOREIGN PATENT DOCUMENTS

| | | |
|---|---|---|
| DE | 37 28 050 A1 | 3/1989 |
| GB | 2 163 457 A | 2/1986 |
| GB | 2273780 A * | 6/1994 |
| JP | 11-352099 * | 12/1999 |

OTHER PUBLICATIONS van Staden et al. (<< Evaluation of different SIA sample-buffer configurations using a fluoride-selective membrane electrode as detector, >> Talanta (2000); 52(1), 3-11).*
JPO English language computer translation of Hiroshi et al. (JP 11-352099 A) Dec. 24, 1999.*
Derwent abstract of Demina et al. (SU 627390 A) Aug. 18, 1978.*
CAPLUS abstract of Brzozka ("Copper membrane electrode based on a macrocyclic thioether," Chemia Analityczna (Warsaw, Poland) (1990), 35(4-5), 415-21).*
CAPLUS abstract of Ion et al. ("Preliminary study regarding thioethers applications in electrodic membranes selective for silver ion," Science and Technology of Environmental Protection (2000).*

* cited by examiner

*Primary Examiner*—Alex Noguerola
(74) *Attorney, Agent, or Firm*—Michael L. Dunn

(57) ABSTRACT

A fluoride-sensitive electrode having a tubular electrode shaft, a lanthanum fluoride crystal, which closes the end of the electrode shaft, an internal electrolyte sealed between the lanthanum fluoride crystal and a closure in the electrode shaft, and a contact wire which dips into the internal electrolyte, wherein the internal electrolyte has a pH of $\geq 9.0$ and a fluoride concentration of $\geq 0.1$ M. The invention also includes the method of using the electrode to determine fluoride ion concentration.

20 Claims, 4 Drawing Sheets

FLUORIDE-SENSITIVE ELECTRODE

BACKGROUND OF THE INVENTION

The invention relates to a fluoride-sensitive electrode and the use of said electrode in measuring the fluoride content of water, in particular in fluoridated drinking water.

In many countries of the world, fluoride is added to drinking water in an amount of about 0.5 to 2 ppm to protect against caries. The fluoride content of drinking water is monitored using fluoride-sensitive electrodes by a potentiometric measurement, as disclosed in 1969 in U.S. Pat. No. 3,431,182. Such electrodes employ lanthanum fluoride as the ion-sensitive element and operate with an internal fluoride-containing electrolyte. The fluoride-sensitive electrode constitutes an electrochemical half-cell which is combined with a conventional reference electrode to determine a potential. If the reference electrode is integrated into the housing of the fluoride-sensitive electrode, it is termed a combination electrode.

Despite their excellent selectivity for fluoride ions, known fluoride-sensitive electrodes exhibit a disturbing cross-sensitivity to hydroxyl ions (OH ions) which increases towards lower fluoride contents. The pH of drinking water or sample water, the fluoride concentration of which is to be determined with the electrode of the invention, will henceforth be termed the "external pH" or "$pH_a$". Since the $pH_a$ of drinking water can lie in the range 6.5 to 9.5 and it is often raised by the supplier to slightly alkaline values in order to make the water less corrosive, for example, this cross-sensitivity to hydroxyl ions disturbs the accuracy of the fluoride-sensitive measuring electrode beyond a $pH_a$ of about 8.5. To overcome this and other cross-sensitivities, TISAB (total ionic strength adjustment buffer) has been used since 1968. The sample water is mixed with TISAB solution to reduce the $pH_a$ of the solution to be measured to about 5.5, inter alia, and thus avoid hydroxyl ion cross-sensitivity. This conditioning of the sample water with TISAB constitutes an additional test costing and in particular, continuous measurement is rendered uneconomical because of the considerable cost of TISAB. Commercially available automated fluoride ion analyzers take samples at selected intervals, mix them with TISAB and then determine the fluoride ion content. Automation using such devices, though, does not avoid the high cost of TISAB.

Thus, the aim of the present invention is to provide a fluoride-sensitive electrode with a lower cross-sensitivity to hydroxyl ions than known electrodes and which also enables accurate measurements of the fluoride content of water with higher $pH_a$ values, in particular at low fluoride concentrations, to be carried out without requiring the use of TISAB.

BRIEF DESCRIPTIONS OF THE INVENTION

The invention provides a fluoride-sensitive electrode of the type defined above with a tubular electrode shaft, a lanthanum fluoride crystal, which closes the end of the electrode shaft, an internal electrolyte sealed between the lanthanum fluoride crystal and a closure in the electrode shaft, and a contact wire which dips into the internal electrolyte, wherein the internal electrolyte has a pH of $\geq 9.0$ and a fluoride concentration of $\geq 0.1$ M. The pH of the internal electrolyte will henceforth be termed the "internal pH" or "$pH_i$". The invention also includes the method of using the electrode to determine fluoride ion concentration.

It has surprisingly been discovered that when using the internal electrolyte of the invention, the hydroxyl ion cross-sensitivity can be reduced to such an extent that the accuracy of the electrode compared with known fluoride-sensitive electrodes is substantially improved even at high values of $pH_a$.

DETAILED DESCRIPTION OF THE INVENTION

Figure 1:
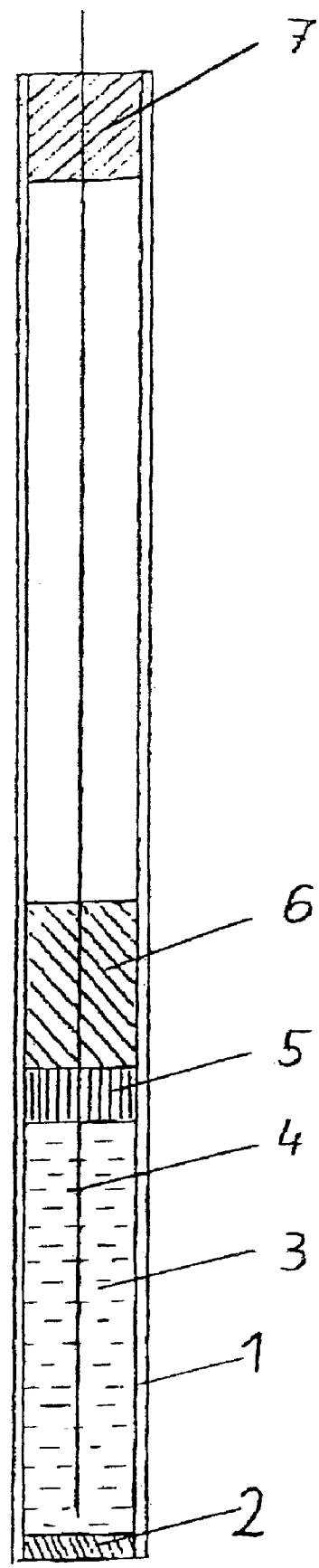
FIG. 1 is a diagrammatic cross section of a fluoride-sensitive electrode of the invention.

A particularly suitable internal electrolyte of the invention contains fluoride ions in the form of sodium fluoride (NaF) in a concentration of $\geq 0.1$ M. Particularly advantageously, the internal electrolyte contains $\geq 1$ M NaCl, preferably $\geq 2$ M NaCl, more preferably $\geq 3$ M NaCl. The $pH_i$ value of said internal electrolyte with added distilled water is preferably adjusted if necessary by adding hydrochloric acid (HCl) or sodium hydroxide solution (NaOH). The use of an internal electrolyte with a $pH_i$ of $\geq 9.0$ in combination with a fluoride concentration of $\geq 0.1$ M in an electrode of the invention is surprisingly far more accurate than known fluoride-sensitive electrodes, and in particular has a lower cross-sensitivity to hydroxyl ions at high pH.

One yardstick indicating the suitability of a fluoride-sensitive electrode is the slope of the curve obtained by plotting the potential (measured in millivolts (mV)) against the concentration of fluoride ions ($c_F$, measured in ppm of fluoride, plotted as log $c_F$). The closer the slope of the curve to the theoretical slope of 59.16 mV/decade at 25° C., the more accurately can the fluoride ion concentration be measured. A further yardstick indicating the suitability of a fluoride-sensitive electrode is the linearity of the curve obtained in the fluoride ion concentration region of interest.

A general problem with electrochemical sensors with a solid electrode, which cannot be ignored and which is also relevant to the fluoride-sensitive electrode of the invention, consists in the fact that the electrochemically effective parts of the electrodes, namely their surfaces, exhibit a certain memory effect. When using an electrode, changes occur at those electrochemically effective surfaces which are themselves electrochemically active and can change the properties of the electrode. This can affect the measured potential and the curve at different fluoride concentrations even when that same electrode is subjected to the same external and internal conditions for different measurements. These surface changes, however, have less effect on the linearity of the potential curve in the fluoride concentration region of interest, but rather on the slope of the curve in this region. Like any other solid electrode, then, with the fluoride-sensitive electrode of the invention it may be advantageous to calibrate the electrode using at least two different fluoride ion concentrations in the concentration region of interest prior to the start of a measurement or a series of measurements. In this respect, it has been shown that changes in the measurement characteristics due to said phenomenon are less significant compared with known fluoride-sensitive electrodes due to the construction of the electrode of the invention and are within acceptable tolerances. Naturally, these tolerances differ from measurement to measurement.

The invention also concerns the use of the fluoride-sensitive electrode of the invention for measuring the fluoride content of water, in particular drinking water supplemented with fluoride.

Particularly advantageously, the electrode of the invention can be used when the $pH_a$ of the drinking water to be measured is $\geq 8.0$ or the $pH_a$ of the drinking water is adjusted to such a value prior to measurement. Compared with known fluoride-sensitive electrodes, the advantages of the electrode of the invention as regards the measurement characteristics only come to light at higher $pH_a$s, as the electrode of the invention is considerably less sensitive to hydroxyl ions than prior electrodes. Thus, the electrode of the invention is advantageously employed at $pH_a$ values of $\geq 8.5$ or $\geq 9.0$ or even at $\geq 9.5$. When the $pH_a$ of the water to be measured is lower, i.e., the $pH_a$ is about 6.0, the electrode of the invention operates as well as known fluoride-sensitive electrodes.

Further advantages, features and embodiments of a particularly preferred implementation of the invention will now be described with reference to the accompanying drawings and examples.

Embodiment of a fluoride-sensitive electrode in accordance with the invention

FIG. 1 shows a particularly preferred construction of an electrode of the invention with a tubular electrode shaft 1, a lanthanum fluoride crystal 2 adhered to the end of the electrode shaft 1 and closing said end, an internal electrolyte 3, which is sealed between the lanthanum fluoride crystal 2 and a closure 5 formed from silicone. A polyurethane sealing compound 6 is also provided above closure 5 to reinforce the seal. The upper end of the electrode shaft 1 is also closed with an airtight seal 7 in order to prevent carbon dioxide in the air from entering the internal electrolyte and changing its pH. A silver/silver chloride contact wire 4 dips into the internal electrolyte and is fed through the silicone closure 5, the polyurethane sealing compound 6 and the upper seal 7 out of the electrode shaft 1. The contact wire is connected to the usual measuring instruments, not shown here. The internal electrolyte 3 has a $pH_i$ of $\geq 9.0$ and a fluoride concentration of $\geq 0.1$ M. In an alternative embodiment, the lanthanum fluoride crystal 2 is not adhered in the electrode shaft 1, but is screwed into it and is thus easy to remove and exchange if the measurement characteristics of the electrode deteriorate due to surface changes in the lanthanum fluoride crystal.

To product the internal electrolyte of the fluoride-sensitive electrode, 3M NaCl and 0.1 M NaF are dissolved in distilled water and the pH is adjusted to the desired value by adding HCl or NaOH.

EXAMPLE 1

Figure 2A:
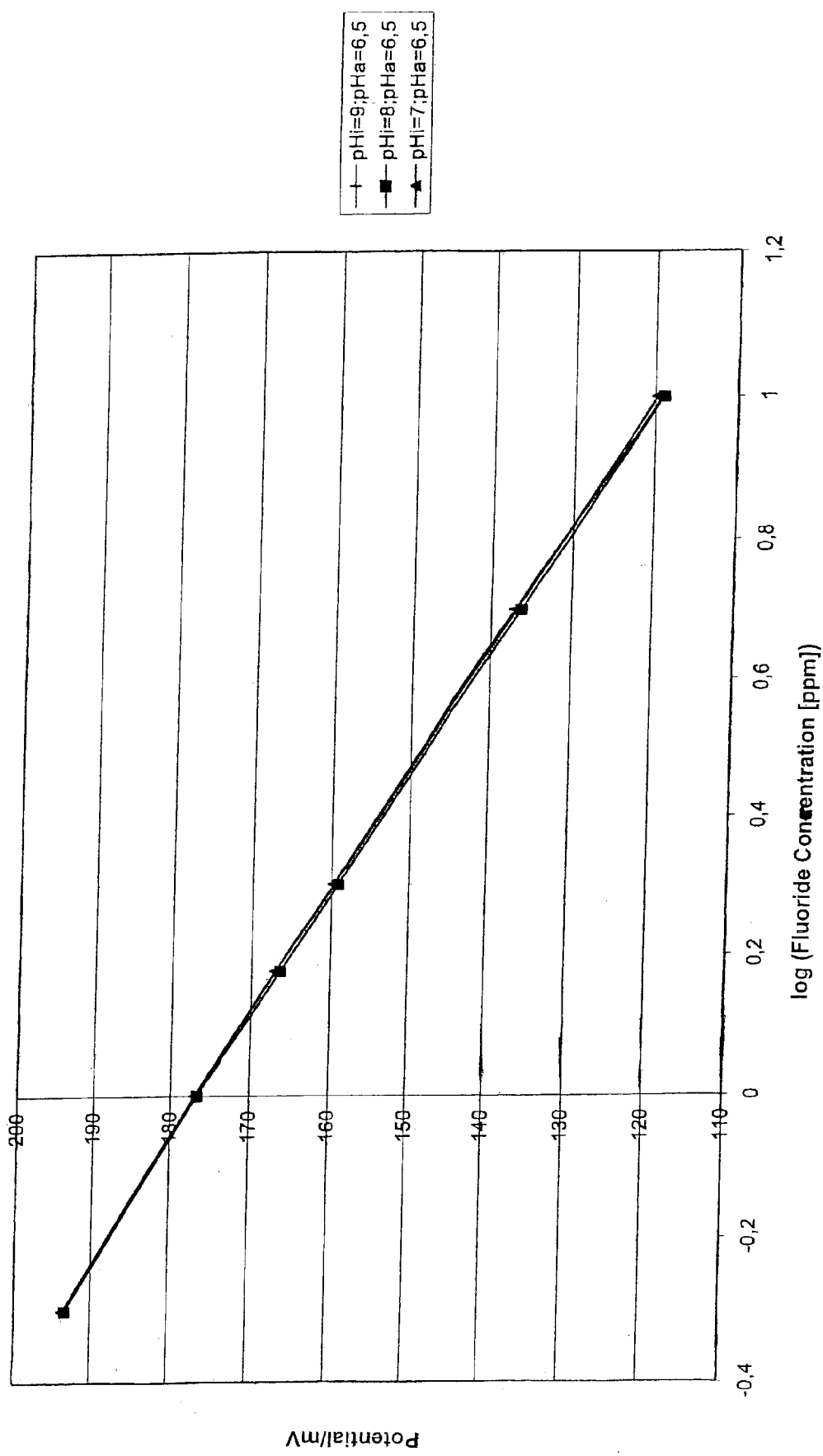
FIGS. 2a, 2b and 3 show the results of series of measurements carried out using the electrode of the invention.
Figure 2B:
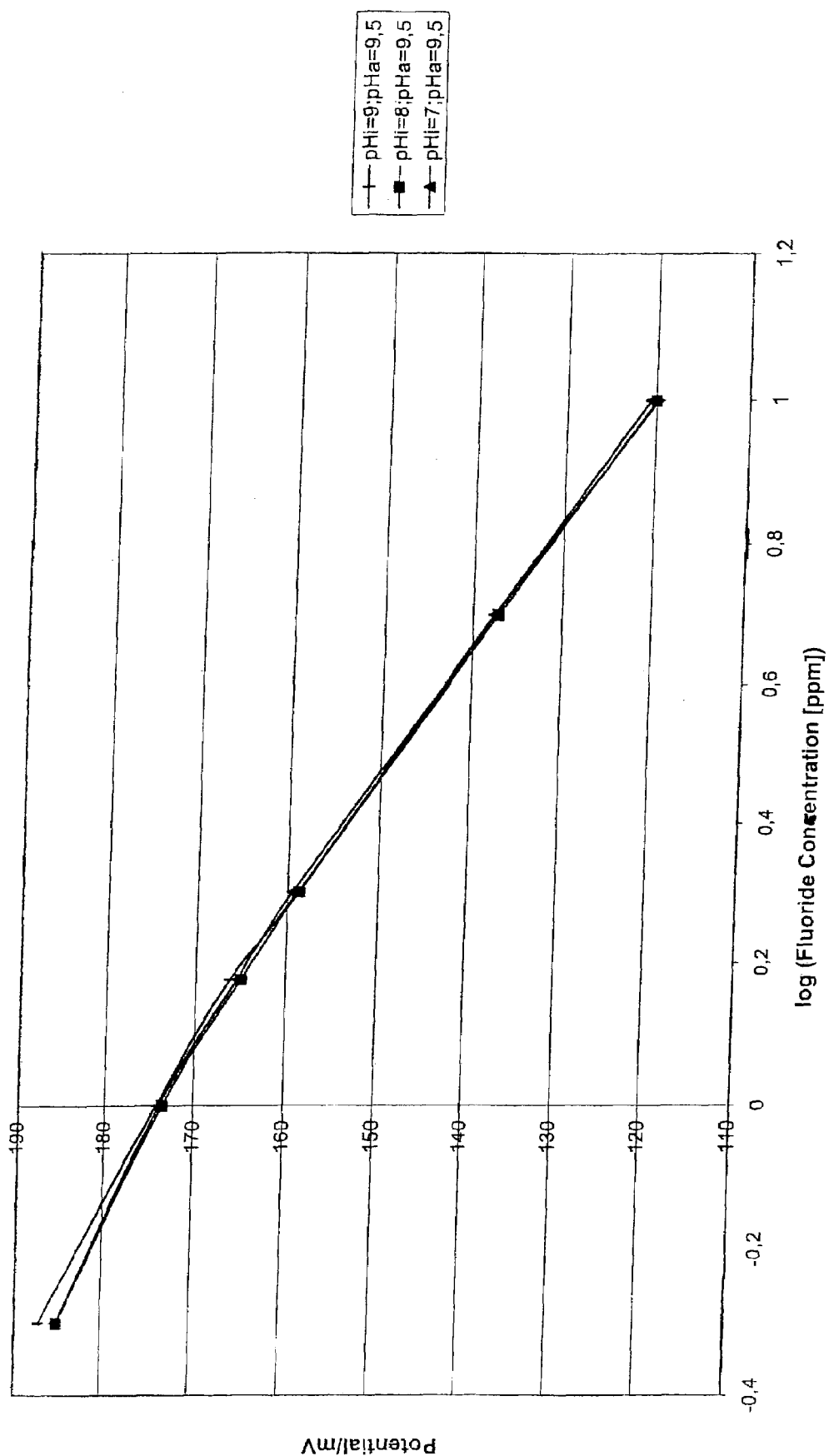

The internal electrolyte used in this example was a solution with 3 M NaCl and 0.1 M NaF in distilled water. The $pH_i$ of the internal electrolyte was adjusted to a $pH_i$ of 7.0, 8.0 or 9.0 by adding HCl or NaOH. Immediately after preparation, the internal electrolyte was poured into the electrode shaft and made airtight by inserting the silicone closure and the polyurethane sealing compound in order to prevent carbon dioxide in the air from changing the $pH_i$. The fluoride-sensitive electrodes formed with the internal electrolyte with different $pH_i$ values was then used to measure the fluoride content in tap water with different values of $pH_a$ from 6.5 to 9.5. Different concentrations of fluoride of 0.5 to 10 ppm of fluoride had been added to the tap water. The results are shown in FIGS. 2a and 2b and in Tables 1 and 2.

The equations for the regression lines clearly showed that an increase in $pH_i$ increased the slopes of the curves both at a $pH_a$ of 6.5 and a $pH_a$ of 9.5.

For the measurements carried out on tap water with a $pH_a$ of 6.5 (Table 1, FIG. 2a), the differences in the curves as regards slope and linearity at low fluoride ion concentrations of 0.5 to 2.0 ppm were only relatively small. With the measurements carried out in tap water at a $pH_a$ of 9.5 (Table 2, FIG. 2b), the electrodes with the highest $pH_i$ for the internal electrolyte ($pH_i=9$) exhibited much better characteristics as regards both the slope and the regression coefficient $R^2$ (a measurement of linearity) than the electrodes with the lower $pH_i$ values ($pH_i=8$, $pH_i=7$). This result was surprising in that no obvious connection should exist between the $pH_i$ and the $pH_a$.

For the lower $pH_a$ of the sample water of 6.5, the electrode of the invention always provided curves with a much better slope and better linearity at low fluoride ion concentrations of 0.5 to 2.0 ppm compared with measurements carried out at a higher $pH_a$ of the sample water of 9.5, like known electrodes with $pH_i$ values for the internal electrolyte of below 9.0 (see FIG. 2a). At the higher $pH_a$ of the sample water of 9.5, however, the advantages of the electrode of the invention with a $pH_i$ of the internal electrolyte that was 9.0 or higher were clear from the better slope and linearity in the lower fluoride ion concentration as opposed to electrodes with a $pH_i$ of the internal electrolyte of less than 9.0 (see FIG. 2b). With all three $pH_i$ values for the internal electrolyte, the curves in FIG. 2b for a $pH_a$ of 9.5 exhibit poorer linearity and a reduction in the slope at low fluoride ion concentrations compared with those of FIG. 2a with a $pH_a$ of 6.5, but at a $pH_i$ of 9, this effect is much smaller than with a lower internal pH, namely a $pH_i$ of 8 or a $pH_i$ of 7.

TABLE 1

Regression equations for sample water with a $pH_a$ of 6.5

| $pH_i$ | Regression equation | Regression coefficient $R^2$ |
|---|---|---|
| $pH_i = 7$ | y = −56.994x + 176.5 | 1 |
| $pH_i = 8$ | y = −57.287x + 176.33 | 1 |
| $pH_i = 9$ | y = −57.298x + 176.81 | 0.9999 |

TABLE 2

Regression equations for sample water with a $pH_a$ of 9.5

| $pH_i$ | Regression equation | Regression coefficient $R^2$ |
|---|---|---|
| $pH_i = 7$ | y = −50.439x + 172.81 | 0.9936 |
| $pH_i = 8$ | y = −50.789x + 172.46 | 0.9944 |
| $pH_i = 9$ | y = −52.280x + 173.64 | 0.9958 |

EXAMPLE 2

Figure 3:
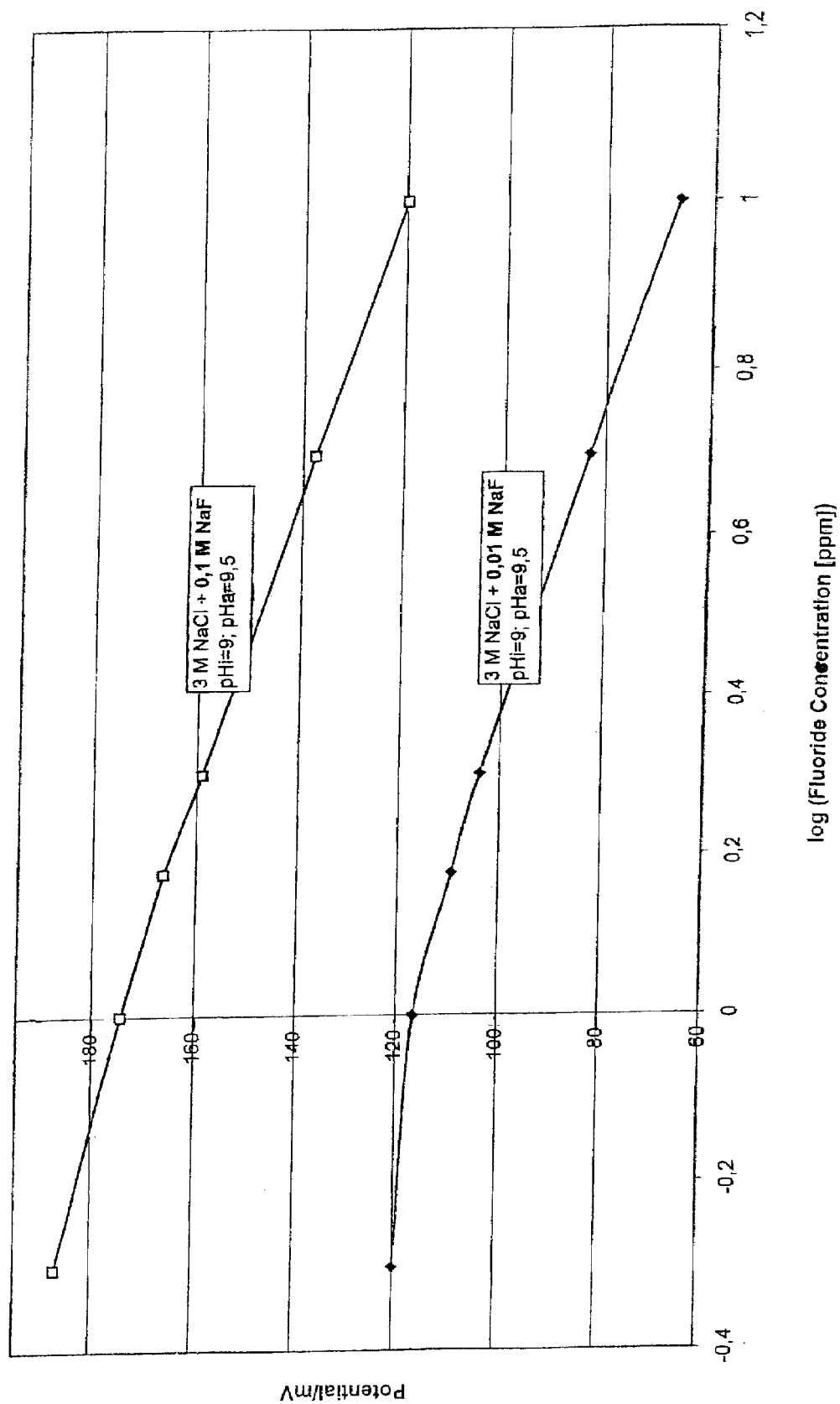

This example compared internal electrolytes with $pH_i$ values of 9.0 each with 3 M NaCl but different fluoride contents of 0.01 M NaF and 0.1 M NaF. Fluoride concentrations in tap water with a $pH_a$ of 9.5 were measured as in Example 1. The results are shown in FIG. 3. the measurements clearly show that the electrodes with the tenfold fluoride content (0.1 M NaF) exhibit better linearity at the lower, critical fluoride concentration region. Further, the slope and regression coefficients $R^2$ were better, as shown in Table 3. Corresponding measurements with a tenfold fluoride content without a corresponding rise in the $pH_i$ value to values of 9.0 or more, however, showed no such improvement (not shown).

The results clearly show that the surprising effect of an improved slope and linearity in the curves at low fluoride concentrations of the sample water is obtained with a combination of using an internal electrolyte with a pH of $\geq 9.0$ and a fluoride concentration of $\geq 0.1$ M.

TABLE 3

Regression equations for sample water with a $pH_a$ of 9.5

| Fluoride concentration | Regression equation | Regression coefficient $R^2$ |
|---|---|---|
| 0.1 M NaF | y = −52.28x + 173.64 | 0.9958 |
| 0.01 M NaF | y = −43.661x + 113.39 | 0.9576 |

What is claimed is:

1. A fluoride-sensitive electrode with a tubular electrode shaft (1), a lanthanum fluoride crystal (2) which closes the end of the electrode shaft (1), an internal electrolyte (3) sealed between the lanthanum fluoride crystal (2) and a closure (5) in the electrode shaft (1), and a contact wire (4) which dips into the internal electrolyte (3), wherein the internal electrolyte (3) has a pH of $\geq 9.0$ and a fluoride concentration of $\geq 0.1$ M.

2. A fluoride-sensitive electrode according to claim 1 wherein the internal electrolyte contains $\geq 0.1$ M NaF.

3. The fluoride-sensitive electrode of claim 2 wherein the internal electrolyte contains from about 1 to about 3 M NaCl.

4. A method for measuring fluoride ion concentrations in sample water which comprises contacting the sample water with the lanthanum fluoride crystal of the electrode of claim 3, measuring potential differences between the water and the internal electrolyte and correlating the measured potential difference with fluoride ion concentration.

5. A method for measuring fluoride ion concentrations in sample water which comprises contacting the sample water with the lanthanum fluoride crystal of the electrode of claim 2, measuring potential differences between the water and the internal electrolyte and correlating the measured potential difference with fluoride ion concentration.

6. A fluoride-sensitive electrode according to claim 1 wherein the internal electrolyte contains at least 1 M NaCl.

7. A method for measuring fluoride ion concentrations in sample water which comprises contacting the sample water with the lanthanum fluoride crystal of the electrode of claim 6, measuring potential differences between the water and the internal electrolyte and correlating the measured potential difference with fluoride ion concentration.

8. The fluoride-sensitive electrode of claim 1 wherein the internal electrolyte contains from about 1 to about 3 M NaCl.

9. A method for measuring fluoride ion concentrations in sample water which comprises contacting the sample water with the lanthanum fluoride crystal of the electrode of claim 8, measuring potential differences between the water and the internal electrolyte and correlating the measured potential difference with fluoride ion concentration.

10. A fluoride-sensitive electrode according to claim 1 wherein the contact wire is a silver/silver chloride contact wire.

11. A method for measuring fluoride ion concentrations in sample water which comprises contacting the sample water with the lanthanum fluoride crystal of the electrode of claim 10, measuring potential differences between the water and the internal electrolyte and correlating the measured potential difference with fluoride ion concentration.

12. A fluoride-sensitive electrode according to claim 1 wherein the closure (5) is formed from an elastomer, preferably a silicone.

13. A method for measuring fluoride ion concentrations in sample water which comprises contacting the sample water with the lanthanum fluoride crystal of the electrode of claim 12, measuring potential differences between the water and the internal electrolyte and correlating the measured potential difference with fluoride ion concentration.

14. A fluoride-sensitive electrode according to claim 1 wherein a sealing compound, preferably a polyurethane sealing compound, is provided above the closure (5) in the electrode shaft (1).

15. A method for measuring fluoride ion concentrations in sample water which comprises contacting the sample water with the lanthanum fluoride crystal of the electrode of claim 14, measuring potential differences between the water and the internal electrolyte and correlating the measured potential difference with fluoride ion concentration.

16. A method for measuring fluoride ion concentrations in sample water which comprises contacting the sample water with the lanthanum fluoride crystal of the electrode of claim 1, measuring potential differences between the water and the internal electrolyte and correlating the measured potential difference with fluoride ion concentration.

17. The method of claim 16 where if the pH of the water is originally less than 8.0 it is upwardly adjusted to a pH of $\geq 8.0$ prior to measurement.

18. The method according to claim 17 wherein the pH of the sample water is at least 9.0.

19. Use according to claim 18, wherein the pH of the sample water is adjusted with HCl or NaOH prior to measurement.

20. Use according to claim 17, wherein the pH of the sample water is adjusted with HCl or NaOH prior to measurement.

* * * * *